United States Patent [19]

Dolnick

[11] Patent Number: 4,769,550
[45] Date of Patent: Sep. 6, 1988

[54] DUAL SCATTERING-TYPE SMOKE DETECTOR WITH CROSS-CHECKING

[75] Inventor: Earl M. Dolnick, Encinitas, Calif.

[73] Assignee: Quantum Group, Inc., San Diego, Calif.

[21] Appl. No.: 79,664

[22] Filed: Jul. 29, 1987

[51] Int. Cl.$^4$ ............................................. G01N 15/06
[52] U.S. Cl. .................................. 250/574; 250/575; 340/630
[58] Field of Search ............... 250/574, 575; 340/630; 356/337, 338, 339, 340, 341, 342, 343

[56] References Cited

U.S. PATENT DOCUMENTS

| | | | |
|---|---|---|---|
| 4,017,193 | 4/1977 | Loiterman | 250/575 |
| 4,647,785 | 3/1987 | Morita | 250/574 |
| 4,695,734 | 9/1987 | Honma et al. | 340/630 |

*Primary Examiner*—David C. Nelms
*Assistant Examiner*—William L. Oen
*Attorney, Agent, or Firm*—Christie, Parker & Hale

[57] ABSTRACT

Two photoelectric smoke detectors are arranged so that each smoke detector in turn verifies operation of the other smoke detector. Each smoke detector has a light source and a photodetector which is not directly illuminated by the light source. A smoke detection signal is issued when light from such a light source is scattered to the respective photodetector. The two smoke detectors are arranged so that a small amount of light from each light source illuminates the photodetector of the other smoke detector. A fault signal is issued when such a photodetector is not illuminated by the other light source.

14 Claims, 2 Drawing Sheets

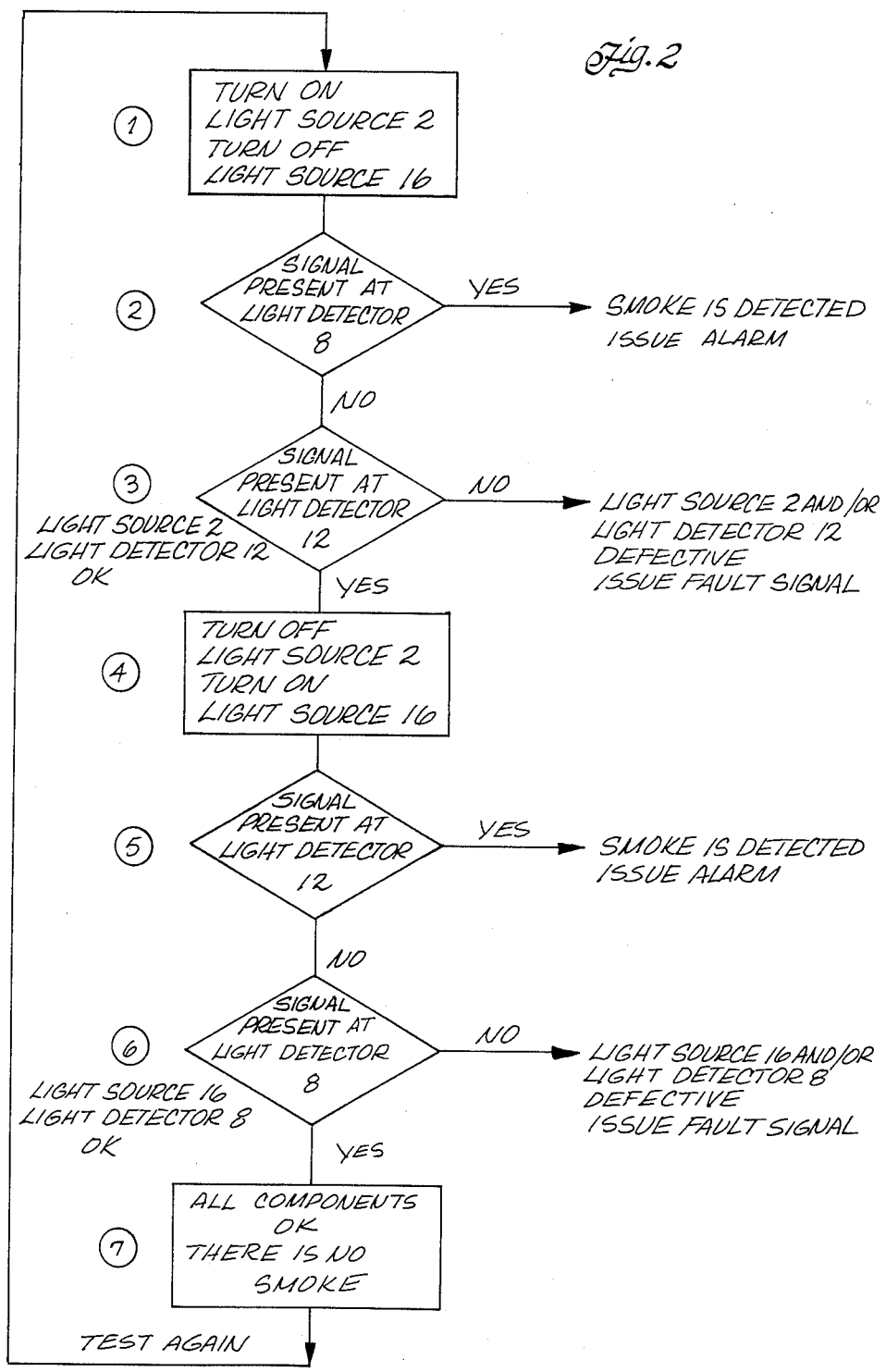

DUAL SCATTERING-TYPE SMOKE DETECTOR WITH CROSS-CHECKING

BACKGROUND OF THE INVENTION

In recent years, the advent of the inexpensive smoke alarm has provided consumers with a simple means of early fire detection. This has resulted in the saving of many lives and in reductions of property damage where fires have occurred.

The present standard for smoke alarms specifies a failure rate of 3.5 failures per million operating hours. While this seems to be a low rate, the huge numbers of devices in service means that a small number of them have failed. There is evidence that among devices more than 10 years old, 20 percent may no longer be functioning, and after 20 years more than 50 percent are likely to have failed. Thus, many thousands of consumers may falsely think they will be warned if smoke appears.

In the typical photoelectric smoke alarm, a darkened volume in communication with the surrounding air is illuminated from one side by a beam of light from a light emitting diode or the like. If smoke is present within the space, some of the light will be scattered perpendicular to the path of the beam. A photodetector is mounted to the side of the darkened space and pointed so that it will detect the scattered light but not the light beam. The photodetector detects light only if particles suspended in the air such as particles of smoke scatter a portion of the light beam. If there is no smoke, there is no scattered light, and hence no signal from the photodetector. This has the advantage that the photodetector and associated circuitry can be operated at high gain, since any signal would be due to smoke. On the other hand there may be no signal because the light source has failed. The photodetector cannot measure the difference. Further, the associated circuitry is unable to tell if the absence of signal may be due to a failed photodetector. Thus, this commonly used method can have several undetectable failure modes which result in failure to detect smoke.

SUMMARY OF THE INVENTION

The invention herein described is a modification of the above described photoelectric smoke detector. Simply described, it is two photoelectric detection systems of conventional design mounted together. They both make measurements for smoke, but by operating them sequentially and alternately, they each also provide test signals for the other to test the other's light detection capability in order to confirm that each is properly operating. This novel method provides for the testing of every component and thus provides a fully failsafe smoke alarm.

THE DRAWINGS

A drawing of one embodiment of the failsafe smoke detector is shown in FIG. 1.

FIG. 2 is a summary of the method in flow chart form.

Figure 1:
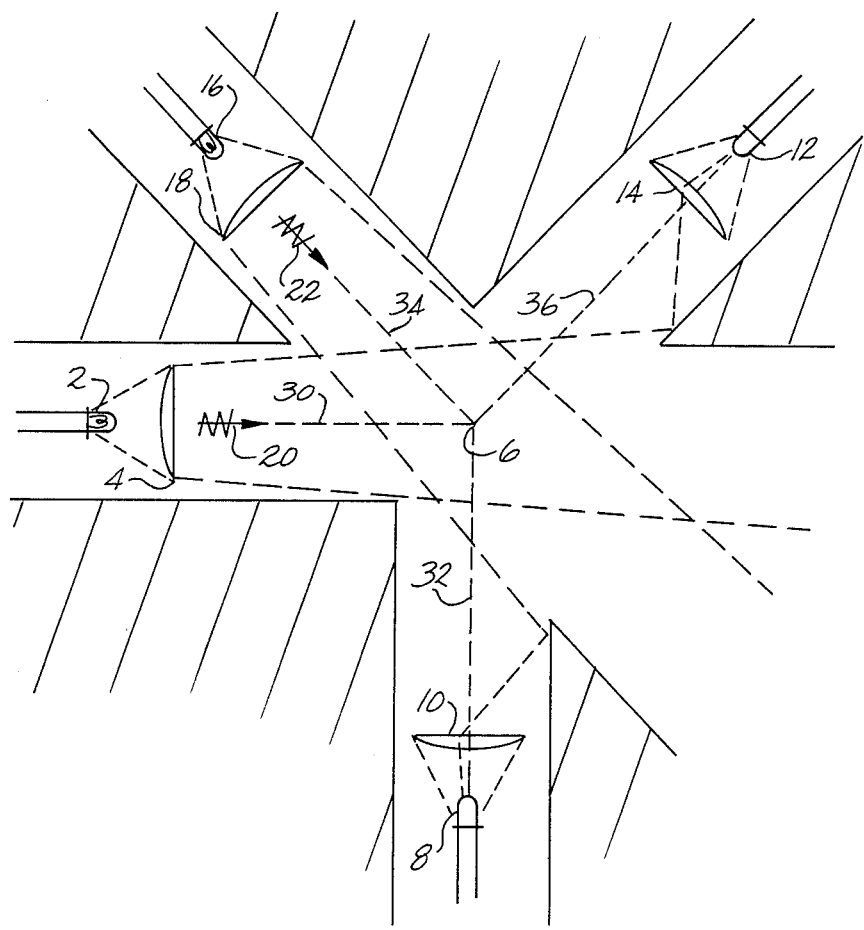
In FIG. 1, a first conventional light source 2 such as a light emitting diode is mounted in front of a first lens 4, along a first common optical axis 30 such that the light emitted by the first light source 2 is collimated by the first lens 4 into a nearly parallel first light beam 20 which slightly diverges as it passes along the first optical axis 30 into a scattering region 6. The scattering region 6 is in communication with the surrounding air in a conventional manner (not shown) but is isolated from ambient light. A first light detector 8, such as a photodiode, is mounted behind a second lens 10 along a second common optical axis 32 at the side of the scattering region 6, and aligned such that their common optical axis 32 is perpendicular to the optical axis 30 of the light source. Light detector 8 and its lens 10 are adjusted such that any light from the scattering region 6 which is scattered in the direction of the second lens 10 is collected and directed to the first light detector 8. It will be recognized that the above components describe a conventional photoelectric smoke alarm.

The remainder of the components comprise another photoelectric smoke alarm similar to the first and mounted in a particular position with respect to the first.

On the other side of the scattering region 6 there is mounted in a similar manner a second light detector 12 placed behind a third lens 14 with their common optical axis 36 pointing to the scattering region 6. The third optical axis 36 is arranged at an angle to the first optical axis 30 such that a small fraction of the light from the sightly divergent first light beam 20 will be collected by the third lens 14 and sensed by the second light detector 12. A second light source 16 is mounted behind a fourth lens 18 and aligned along a fourth common optical axis 34 so that a slightly divergent second light beam 22 emerges and passes along the optical axis 34 to the scattering region 6. The position of the second light source 16 and the fourth lens 18 are arranged so that their optical axis 34 makes a right angle with the third optical axis 36. By symmetry, it can be easily seen that a small fraction of the light from the second light beam 22 will be sensed by the first light detector 8 in the same manner that a small portion of the first light beam 20 will be sensed by the second light detector 12. The lenses are employed to allow small area light sources and light detectors to work over large areas. If large area light sources and/or light detectors are used, the lenses may not be necessary. The scattering region 6 may either be a seperate region for each of the two smoke detectors or they may be combined into the same volume as illustrated.

The smoke detector works in the following manner; Assume that there is no smoke within the scattering region 6, and all light sources are off. The first light source 2 is turned on and the resilient light is collimated by its lens 4 into a slightly diverging beam of light which passes into the scattering region 6. Since there is no smoke, no light is scattered, and no light is detected by the first light detector 8. However, a small portion of the edge of the first light beam 20 passes to the third lens 14 and is detected by the second light detector 12. Thus, the signal from the second light detector 12 confirms that the first light source 2 and the second light detector 12 are properly operating. The absense of signal from the first light detector 8 indicates that either the first light detector 8 detects no smoke or is not functional.

Now, turn off the first light source 2, and turn on the second light source 16. In the same manner as described above, the light from the second light source 16 is collimated into a nearly parallel beam 22 and passed into the scattering region 6. If there were no smoke, the second light detector 10 would detect no signal. Since the second light detector 12 was already tested, either the second light source 16 is not functioning or there is no smoke.

In the same manner as above the first light detector 8 detects a small portion of the second light beam 22. This confirms that the second light source 16 is operating, and the first light detector 8 must then also be operating. Therefore, by the first test result, there is no smoke. In addition since the second light source 16 was found to be functioning by the second test and the second light detector 12 was found to be good by the first test, no signal from the second light detector 12 during the second test confirms that there is no smoke.

The angle between the two smoke detector assemblies is chosen so that when either light detector is used to confirm the light source of the other, the light intensity used is the same as the intensity that the light detector would see if it were to see light scattered by smoke. Thus, the light detectors and associated circuitry (not shown) are confirmed to operate at the same threshold levels necessary for the detection of smoke.

The smoke alarm assemblies need not be restricted to use right angle scattering. Any geometric arrangement could be used as long as the two assemblies are linked such that the proper intensity test signals are produced. Since the test signals are a fixed portion of the generated beams, they may be used with appropriate circuitry to regulate the beam intensity of each light source, if such regulation is desired.

In the arrangement illustrated in FIG. 1, a slightly diverging light beam is used. An alternative arrangement has a collimated light beam and simply offsets the photodetectors to receive a suitable small amount of illumination from the light source to be tested. Mirrors or fiber optic light guides may also be used to pick up a small amount of light and direct it to the proper photodetector. Such an embodiment provides an easy way for illuminating the photodetector with light approximately equal to the light scattered by smoke at the threshold of detection.

The first test determines that the first light source 2 and the second light detector 12 are functioning, and the second test determines that the second light source 16 and the first light detector 8 also function. Thus, all components are tested, and the presence or absence of smoke is determined in a redundant manner. If desired, the alarm circuit may be arranged to require that both smoke alarm channels indicate smoke before an alarm is issued. This increases the reliability and enhances the false alarm resistance.

FIG. 2 is a summary of the method of operating the self checking smoke detector in flow chart form. Conventional logic elements are used to implement the method which is comprised of seven steps:

1. Turn on first light source 2 and leave second light source 16 turned off.
2. Is signal present from first light detector 8?
    A. Yes—smoke is present—issue alarm.
    B. No—continue with step 3.
3. Is signal present from second light detector 12?
    A. No—first light source 2 is defective—issue advisory.
    B. Yes—continue with step 4.
4. Turn on second light source 16 and turn off first light source 2.
5. Is signal present from second light detector 12?
    A. Yes—Smoke present—issue alarm.
    B. No—Continue with step 6.
6. Is signal present from first light detector 8?
    A. No—second light source 16 is defective—issue advisory.
    B. Yes—continue with step 7.
7. Therefore, all components are functional and there is no smoke.

Go to Step 1

This latter step may have a moderate delay before repeating the testing and detection cycle as is conventional.

Thus, a method of operating two photoelectric smoke detectors has been described which links the two in such a manner that they test each other for proper operation, in addition to testing for the presence of smoke. Thus, the two comprise a photoelectric smoke detector which is both redundant and fail safe.

What is claimed is:

1. A smoke detector comprising:
    a first light source;
    a first photodetector out of alignment with the first light source for detecting scattered light from the first light source;
    a second light source not aligned with either the first light source or the first photodetector and arranged so that a fraction of its light illuminates the first photodetector; and
    a second photodetector not aligned with either the first light source or the first photodetector or the second light source for detecting scattered light from the second light source and arranged for illumination by a fraction of the light from the first light source.

2. A smoke detector as recited in claim 1 further comprising means for sequentially and alternately activating the first light source and the second light source.

3. A smoke detector as recited in claim 1 wherein the intensity of light from the first light source illuminating the second photodetector is in the same order as light scattered from the second light source to the second photodetector at the threshold for detecting smoke.

4. A smoke detector as recited in claim 1 comprising means for issuing a smoke alarm when either light from the first light source is scattered to the first photodetector or light from the second light source is scattered to the second photodetector.

5. A smoke detector as recited in claim 1 comprising means for issuing a smoke alarm when light from the first light source is scattered to the first photodetector and light from the second light source is scattered to the second photodetector.

6. A smoke detector as recited in claim 1 wherein the first light source and second light source both illuminate the same smoke detection volume.

7. A smoke detector as recited in claim 1 comprising means for issuing a fault signal when either no light from the first light source is detected by the second photodetector or no light from the second light source is detected by the first photodetector.

8. A self-checking smoke detector comprising:
    a first photoelectric smoke detector comprising a first light source and a first photodetector for detecting light from the first light source scattered from smoke in a scattering region;
    a second photoelectric smoke detector comprising a second light source and a second photodetector for detecting light from the second light source scattered from smoke in a scattering region; and the first and second smoke detectors being positioned so that light from each smoke detector tests the photodetector of the other smoke detector.

9. A smoke detector as recited in claim 8 wherein the scattering region for the first smoke detector is the same as the scattering region for the second smoke detector.

10. A smoke detector as recited in claim 8 wherein the light from each smoke detector to the photodetector of the other smoke detector is in the same order of intensity as light scattered from smoke in the scattering region toward the respective photodetector.

11. A smoke detector as recited in claim 8 comprising means for alternately activating the first and second smoke detectors.

12. A smoke detector as recited in claim 11 comprising means for generating a fault signal when either the second photodetector fails to detect light from the first light source or the first photodetector fails to detect light from the second light source.

13. A smoke detector as recited in claim 12 comprising means for issuing a smoke alarm when either the first smoke detector or the second smoke detector detects smoke.

14. A failsafe smoke detector comprising:
a first photoelectric smoke detector circuit;
a second photoelectric smoke detector circuit;
means for testing operation of the first smoke detector circuit with the second smoke detector circuit; and
means for testing operation of the second smoke detector circuit with the first smoke detector circuit.

* * * * *